(12) United States Patent
Wardleworth et al.

(10) Patent No.: US 6,777,438 B2
(45) Date of Patent: Aug. 17, 2004

(54) INHIBITORS OF FARNESYL PROTEIN TRANSFERASE

(75) Inventors: James Michael Wardleworth, Macclesfield Cheshire (GB); Francis Thomas Boyle, Macclesfield Cheshire (GB); Zbigniew Matusiak, Macclesfield Cheshire (GB)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 10/168,379

(22) PCT Filed: Dec. 18, 2000

(86) PCT No.: PCT/GB00/04875

§ 371 (c)(1),
(2), (4) Date: Jun. 20, 2002

(87) PCT Pub. No.: WO01/46138

PCT Pub. Date: Jun. 28, 2001

(65) Prior Publication Data

US 2003/0096842 A1 May 22, 2003

(30) Foreign Application Priority Data

Dec. 22, 1999 (GB) .............................................. 9930317

(51) Int. Cl.$^7$ ...................... A61K 31/40; C07D 207/04
(52) U.S. Cl. ...................... 514/424; 548/541
(58) Field of Search ............................... 514/326, 378, 514/424, 473; 546/208, 278.4; 548/240, 541; 549/472

(56) References Cited

U.S. PATENT DOCUMENTS

| | | | |
|---|---|---|---|
| 5,185,248 A | 2/1993 | Barbacid et al. | |
| 5,478,820 A | 12/1995 | Betts et al. | |
| 6,232,338 B1 | 5/2001 | Davies et al. | |
| 6,414,145 B1 | 7/2002 | Boyle et al. | |
| 6,541,491 B1 | 4/2003 | Davies et al. | |

FOREIGN PATENT DOCUMENTS

| | | |
|---|---|---|
| EP | 0 126 587 A1 | 11/1984 |
| EP | 0 182 213 A1 | 5/1986 |
| EP | 0 272 456 A1 | 6/1988 |

(List continued on next page.)

OTHER PUBLICATIONS

U.S. application Ser. No. 09/509,210, Arnould, filed Mar. 24, 2000.
U.S. application Ser. No. 09/869,064, Arnould, filed Jun. 21, 2001.
U.S. application Ser. No. 10/110,690, Wardleworth et al., filed Apr. 17, 2002.
Evans et al., "Nanomolar–Affinity, Non–Peptide Oxytocin Receptor Antagonists," J. Med. Chem., vol. 36, No. 25, 1993, pp. 3993–4005.
Garcia et al., "Peptidomimetic Inhibitors of Ras Farnesylation and Function in Whole Cells", J. Biol. Chem., vol. 268, 1993, pp. 18415–18418.
Graham t al., "Pseudopeptide Inhibitors of Ras Farnesyl–Protein Transferase", J. Med. Chem. 1994; vol. 37, pp. 725–732.
Kemp et al., "Studies of N–Terminal Templates for a–Helix Formation: Synthesis and Conformational Analysis of (2S, 5S,8S,11S)–1–Acetyl–1,4–diaza–3–keto– 5 – carboxy– 10– thiatricyclo[2.8.1.0$^{4.8}$]–tridecane (Ac–Hel$_1$–OH)", J. Org. Chem., 1991, vol. 56, pp. 6672–6682.
Kohl et al., "Selective Inhibition of ras–Dependent Transformation by Farnesyltransferase inhibitor", Science, vol. 260, Jun. 25, 1993, pp. 1934–1937.
Lerner et al.; "Ras CAAX Petpidomimetric FT1–277 S lectively Blocks Oncogenic . . . Inactive Ras–Faf Complexes"; The Journal of Biological Chemistry, vol. 270, Nov. 1995, pp. 26802–26806.
Magolda et al., "Design and Synthesis of Conformationally Restricted Phospholipids as Phospholipase A2 Inhibitors", J. Cellular Biochemistry, 1989, vol. 40, pp. 371–386.
Matsumura et al., "An Efficient Synthesis of (2S,4S)–Substituted 4–Mercaptopyrrolidine Derivatives", Heterocycles, vol. 41, No. 1, 1995, pp. 147–159.
Sunagawa et al., "A Novel Carbapenem Antiobiotic, SM–7338 Structure–Activity Relationships", J. Antibiotics, vol. XLIII, No. 5, 1990, pp. 519–532.
Sunagawa et al., "Synthesis and Antibacterial Activity of Novel Carbapenems with a Catechol of Hydroxypyridone Moiety", J. Antibiotics, vol. 47, No. 11, 1994, pp. 1354–1358.

Primary Examiner—Taofiq Solola
(74) Attorney, Agent, or Firm—Morgan, Lewis & Bockius LLP

(57) ABSTRACT

This invention relates to compounds of formula (I) that inhibit farnesylation of gene products through inhibition of the enzyme farnesyl-protein transferase (FPTase). The invention also relates to methods of manufacturing the compounds, pharmaceutical compositions and methods of treating diseases, especially cancer, which are mediated through farnesylation.

(I)

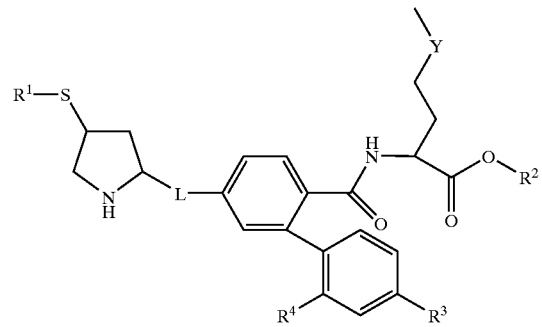

23 Claims, No Drawings

FOREIGN PATENT DOCUMENTS

| | | |
|---|---|---|
| EP | 0 280 771 | 9/1988 |
| EP | 0 442 497 | 8/1991 |
| EP | 0 443 883 | 8/1991 |
| EP | 0 508 682 | 10/1992 |
| EP | 0 518 558 | 12/1992 |
| EP | 0 521 524 A1 | 1/1993 |
| EP | 0 537 007 A1 | 4/1993 |
| EP | 0 560 613 A1 | 9/1993 |
| EP | 0 562 855 | 9/1993 |
| EP | 0 581 500 A1 | 2/1994 |
| EP | 0 581 501 B1 | 2/1994 |
| EP | 0 581 502 B1 | 2/1994 |
| EP | 0 590 885 B1 | 4/1994 |
| EP | 0 592 167 | 4/1994 |
| EP | 0 618 221 A2 | 10/1994 |
| EP | 0 696 593 A2 | 2/1996 |
| JP | 60-233076 | 11/1985 |
| WO | 92/17479 | 10/1992 |
| WO | 92/17480 | 10/1992 |
| WO | 93/15078 | 8/1993 |
| WO | 93/19070 | 9/1993 |
| WO | 93/21186 | 10/1993 |
| WO | 94/04561 | 3/1994 |
| WO | 95/00497 | 1/1995 |
| WO | 95/09000 | 4/1995 |
| WO | 95/09001 | 4/1995 |
| WO | 95/25086 | 9/1995 |
| WO | 96/09821 | 4/1996 |
| WO | 97/05135 | 2/1997 |
| WO | WO 97/06138 | 2/1997 |
| WO | 98/07692 | 2/1998 |
| WO | 98/32741 | 7/1998 |
| WO | WO 98/50029 | 11/1998 |
| WO | 99/20611 | 4/1999 |
| WO | WO 99/41235 | 8/1999 |
| WO | 00/39716 | 7/2000 |
| WO | 01/46317 | 6/2001 |

INHIBITORS OF FARNESYL PROTEIN TRANSFERASE

This application is a 371 of PCT/GB00/04875 filed Dec. 18, 2000.

This invention relates to compounds that inhibit farnesylation of mutant ras gene products through inhibition of the enzyme farnesyl-protein transferase (FPTase). The invention also relates to methods of manufacturing the compounds, pharmaceutical compositions and methods of treating diseases, especially cancer, which are mediated through farnesylation.

Cancer is believed to involve alteration in expression or function of genes controlling cell growth and differentiation. Whilst not wishing to be bound by theoretical considerations the following text sets out the scientific background to ras in cancer. Ras genes are frequently mutated in tumours. Ras genes encode guanosine triphosphate (GTP) binding proteins which are believed to be involved in signal transduction, proliferation and malignant transformation. H-, K- and N-ras genes have been identified as mutant forms of ras (Barbacid M, Ann. Rev. Biochem. 1987, 56: 779–827). Post translational modification of ras protein is required for biological activity. Farnesylation of ras catalysed by FPTase is believed to be an essential step in ras processing. It occurs by transfer of the farnesyl group of farnesyl pyrophosphate (FPP) to a cysteine at the C-terminal tetrapeptide of ras in a structural motif called the CAAX box. After further post-translational modifications, including proteolytic cleavage at the cysteine residue of the CAAX box and methylation of the cysteine carboxyl, ras is able to attach to the cell membrane for relay of growth signals to the cell interior. In normal cells activated ras is believed to act in conjunction with growth factors to stimulate cell growth. In tumour cells it is believed that mutations in ras cause it to stimulate division even in the absence of growth factors (Travis J. Science 1993, 260: 1877–1878), possibly through being permanently in GTP activated form rather than cycled back to GDP inactivated form. Inhibition of farnesylation of mutant ras gene products will stop or reduce activation.

One class of known inhibitors of farnesyl transferase is based on farnesyl pyrophosphate analogues; see for example European patent application EP 534546 from Merck. Inhibitors of farnesyl transferase based on mimicry of the CAAX box have been reported. Reiss (1990) in Cell 62, 81–8 disclosed tetrapeptides such as CVIM (Cys-Val-Ile-Met). James (1993) in Science 260, 1937–1942 disclosed benzodiazepine based peptidomimetic compounds. Lerner (1995) in J. Biol. Chem. 270, 26802 and Eisai in International Patent Application WO 95/25086 disclosed further peptidomimetic compounds based on Cys as the first residue. EP 696593 and PCT/GB96/01810 disclose further farnesyl transferase inhibitors, including pyrrolidine derivatives.

The applicants have found that a particular substitution of the pyrrolidine provides particular advantages in terms of inhibition of farnesyl transferase.

According to one aspect of the present invention there is provided a compound of formula (I):

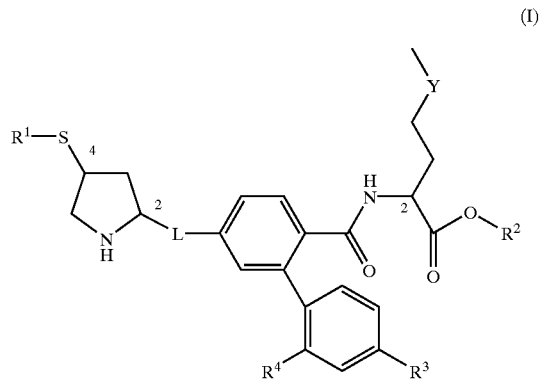

wherein:
$R^1$ and $R^2$ are independently selected from H or a prodrug moiety;
$R^3$ is hydrogen or halogen;
$R^4$ is hydrogen or halogen;
L is —CH=CH— or —CH$_2$—Z— where Z is NH or O;
Y is S, S(O) or S(O)$_2$;
or a salt thereof, provided that at least one of $R^3$ or $R^4$ is other than hydrogen.

As used herein, the term "alkyl" refers to straight or branched chain groups, which may, unless otherwise stated have from 1 to 20 and preferably from 1 to 6 carbon atoms. The term "aryl" includes phenyl. The term "halo" includes fluoro, chloro, bromo and iodo.

The term "heterocyclyl" or "heterocyclic" include groups having from 4 to 10 ring atoms, up to 5 of which are selected from oxygen, sulphur and nitrogen. The rings may be mono-, or bicyclic and each ring may be aromatic or non-aromatic in character. Nitrogen atoms may be substituted if the valency of the ring allows it, with either a hydrogen or substituent group, such as a alkyl substituent. Sulphur atoms in a heterocyclic ring may be oxidised to S(O) or S(O)$_2$ groups.

Examples of aromatic 5- or 6-membered heterocyclic ring systems include imidazole, triazole, pyrazine, pyrimidine, pyridazine, pyridine, isoxazole, oxazole, isothiazole, thiazole and thiophene. A 9- or 10-membered bicyclic heteroaryl ring system is an aromatic bicyclic ring system comprising a 6-membered ring fused to either a 5 membered ring or another 6 membered ring. Examples of 5/6 and 6/6 bicyclic ring systems include benzofuran, benzimidazole, benzthiophene, benzthiazole, benzisothiazole, benzoxazole, benzisoxazole, pyridoimidazole, pyrimidoimidazole, quinoline, isoquinoline, quinoxaline, quinazoline, phthalazine, cinnoline and naphthyridine.

Preferably monocyclic heteroaryl rings contain up to 3 heteroatoms and bicyclic heteroaryl rings contain up to 5 heteroatoms. Preferred heteroatoms are N and S, especially N. In general, attachment of heterocyclic rings to other groups is via carbon atoms. Suitable heterocyclic groups containing only N as the heteroatom are pyrrole, pyridine, indole, quinoline, isoquinoline, imidazole, pyrazine, pyrimidine, purine and pteridine.

Hydrogenated or other substituted forms of the above aromatic rings, (which are not aromatic), such as tetrahydropyridyl rings are examples of non-aromatic heterocyclic groups.

Various forms of prodrugs are known in the art. For examples of such prodrug derivatives, see:

a) Design of Prodrugs, edited by H. Bundgaard, (Elsevier, 1985) and Methods in Enzymology, Vol. 42, p. 309–396, edited by K. Widder, et al. (Academic Press, 1985);
b) A Textbook of Drug Design and Development, edited by Krogsgaard-Larsen;
c) H. Bundgaard, Chapter 5 "Design and Application of Prodrugs", by H. Bundgaard p. 113–191 (1991);
d) H. Bundgaard, Advanced Drug Delivery Reviews, 8, 1–38 (1992);
e) H. Bundgaard, et al., Journal of Pharmaceutical Sciences, 77, 285 (1988); and
f) N. Kakeya, et al., Chem Pharm Bull, 32, 692 (1984).

Suitable examples of groups $R^1$ are hydrogen or prodrug groups of formula $R^5C(O)$— where $R^5$ is an optionally substituted aryl or heterocyclyl group. In particular $R^5$ is optionally substituted phenyl, optionally substituted pyridyl optionally substituted furyl, optionally substituted isoxazole, optionally substituted tetrahydropyridyl or optionally substituted tetrahydrofuryl.

Suitable substituents for $R^5$ include alkyl groups such as methyl, haloalkyl groups such as trifluoromethyl, hydroxy, alkoxy such as methoxy or cyano.

Preferably $R^5$ is phenyl, pyridyl or N-methyl-tetrahydropyridyl.

Examples of prodrugs groups for $R^2$ are in vivo cleavable ester groups of a pharmaceutically-acceptable ester which is cleaved in the human or animal body to produce the parent acid. Suitably $R^2$ together with the carboxy group to which it is attached forms a pharmaceutically-acceptable esters such as $C_{1-6}$alkyl esters or $C_{1-6}$cycloalkyl esters, for example methyl, ethyl, propyl, iso-propyl, n-butyl or cyclopentyl; $C_{1-6}$alkoxymethyl esters, for example methoxymethyl; $C_{1-6}$alkanoyloxymethyl esters, for example pivaloyloxymethyl; phthalidyl esters; $C_{3-8}$cycloalkoxycarbonyloxy$C_{1-6}$alkyl esters, for example 1-cyclohexylcarbonyloxyethyl; 1,3-dioxolan-2-ylmethyl esters, for example 5-methyl-1,3-dioxolan-2-ylmethyl; $C_{1-6}$alkoxycarbonyloxyethyl esters, for example 1-methoxycarbonyloxyethyl; aminocarbonylmethyl esters and mono- or di-N—($C_{1-6}$alkyl) versions thereof, for example N,N-dimethylaminocarbonylmethyl esters and N-ethylaminocarbonylmethyl esters, and pharmaceutically acceptable esters of optionally substituted heterocyclic groups.

Further examples of such prodrugs for $R^2$ are in vivo cleavable amides of a compound of the invention. Suitably $R^2$ together with the carboxy group to which it is attached forms a pharmaceutically-acceptable amide, preferably an N—$C_{1-6}$alkylamide and an N,N-di-($C_{1-6}$alkyl)amide, such as N-methyl, N-ethyl, N-propyl, N,N-dimethyl, N-ethyl-N-methyl or N,N-diethylamide.

Thus in particular, $R^2$ is selected from hydrogen, a $C_{1-4}$alkyl group such as isopropyl or cyclopentyl, or an optionally substituted heterocyclic group such as N-methyl-tetrahydropyridyl.

$R^3$ is suitably a halo atom such as fluoro or chloro group, in particular fluorine.

$R^4$ is preferably a hydrogen or fluorine, and in particular is hydrogen.

The linking group L is suitably a group of formula $CH_2$—Z— where Z is NH or O.

Preferably the linking group L is —CH=CH—. Both E and Z isomeric forms of such compounds form part of the invention together with mixtures thereof. In particular, compounds were geometrical isomerism is possible are preferably in E form.

Group Y is preferably a group S or $S(O)_2$.

It is to be understood that, insofar as certain of the compounds of Formula I defined above may exist in optically active or racemic forms by virtue of one or more asymmetric carbon atoms, the invention includes in its definition any such optically active or racemic form which possesses the property of inhibiting FTPase. The synthesis of optically active forms may be carried out by standard techniques of organic chemistry well known in the art, for example by synthesis from optically active starting materials or by resolution of a racemic form. Similarly, inhibitory properties against FTPase may be evaluated using the standard laboratory techniques referred to hereinafter.

Chiral carbon atoms at the 2 and 4 positions of the pyrrolidine ring in Formula I are preferred in the (S) configuration.

The chiral carbon atom at the 2 position between the carbonyl and amine in Formula I is preferred in the (S) configuration.

Compounds of Formula I may form salts which are within the ambit of the invention. Pharmaceutically acceptable salts are preferred although other salts may be useful in, for example, isolating or purifying compounds.

When the compound contains a basic moiety it may form pharmaceutically acceptable salts with a variety of inorganic or organic acids, for example hydrochloric, hydrobromic, sulphuric, phosphoric, trifluoroacetic, citric or maleic acid. A suitable pharmaceutically-acceptable salt of the invention when the compound contains an acidic moiety is an alkali metal salt, for example a sodium or potassium salt, an alkaline earth metal salt, for example a calcium or magnesium salt, an ammonium salt or a salt with an organic base which affords a pharmaceutically-acceptable cation, for example a salt with methylamine, dimethylamine, trimethylamine, piperidine, morpholine or tris-(2-hydroxyethyl)amine. Particular salts of compounds of the invention are acetates, alkyl sulphonates such as methyl or ethyl sulphonate, fumarates, formates, succinates and gluconates.

Solvates, for example hydrates, are also within the ambit of the invention and may be prepared by generally known methods.

Particular examples of compounds of formula (I) are shown in Table 1

TABLE 1

| Compd. No | R¹ | R² | R³ | L | Y |
|---|---|---|---|---|---|
| 1 | H | H | F | —CH=CH— (E form) | S |
| 2 | H | 4-methyl-N-methylpiperidinyl | F | —CH=CH— (E form) | S |
| 3 | H | —CH(CH$_3$)$_2$ | F | —CH=CH— (E form) | S |
| 4 | phenyl-C(O)— | 4-methyl-N-methylpiperidinyl | F | —CH$_2$O— | S |
| 5 | (1-methylpiperidin-4-yl)-C(O)— | —CH(CH$_3$)$_2$ | F | —CH=CH— (E form) | S |
| 6 | H | H | F | —CH$_2$NH— | S |
| 7 | H | —CH(CH$_3$)$_2$ | F | —CH$_2$NH— | S |
| 8 | (1-methylpiperidin-4-yl)-C(O)— | —CH(CH$_3$)$_2$ | F | —CH$_2$NH— | S |
| 9 | (pyridin-3-yl)-C(O)— | 4-methyl-N-methylpiperidinyl | F | —CH=CH— | S |

According to another aspect of the invention there is provided a compound of Formula I for use as a medicament.

Further according to the invention there is provided a compound of Formula I for use in preparation of a medicament for treatment of a disease mediated through farnesylation of ras, in particular cancer.

The compound is suitably formulated as a pharmaceutical composition for use in this way.

Thus, according to yet another aspect of the invention there is provided a pharmaceutical composition comprising a compound of formula I listed above together with a pharmaceutically acceptable diluent or carrier.

According to another aspect of the present invention there is provided a method of treating ras mediated diseases, especially cancer, by administering an effective amount of a compound of Formula I to a mammal in need of such treatment.

According to a further feature of the invention there is provided a compound of Formula I, or a pharmaceutically-acceptable salt thereof, for use in a method of treatment of the human or animal body by therapy.

The invention also provides the use of a compound of formula (I) in the preparation of a medicament for use in treating farnesylated ras mediated disease or medical condition such as cancers.

Specific cancers which may be treated by the compound or composition of the invention include:

carcinoma, including that of the bladder, breast, colon, kidney, liver, lung, ovary, pancreas, stomach, cervix, thyroid and skin;

hematopoietic tumors of lymphoid lineage, including acute lymphocytic leukemia, B-cell lymphoma and Burketts lymphoma;

hematopoietic tumors of myeloid lineage, including acute and chronic myelogenous leukemias and promyelocytic leukemia;

tumors of mesenchymal origin, including fibrosarcoma and rhabdomyosarcoma; and other tumors, including melanoma, seminoma, tetratocarcinoma, neuroblastoma and glioma.

The compounds of Formula I are especially useful in treatment of tumors having a high incidence of ras mutation, such as colon, lung, and pancreatic tumors. By the administration of a composition having one (or a combination) of the compounds of this invention, development of tumors in a mammalian host is reduced.

Compounds of Formula I may also be useful in the treatment of diseases other than cancer that may be associated with signal transduction pathways operating through Ras, e.g., neuro-fibromatosis.

Compounds of Formula I may also be useful in the treatment of diseases associated with CAAX-containing proteins other than Ras (e.g., nuclear lamins and transducin) that are also post-translationally modified by the enzyme farnesyl protein transferase.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

Suitable pharmaceutically acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate; anti-oxidants (such as ascorbic acid), colouring agents, flavouring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavouring and colouring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavouring and preservative agents.

Syrups and elixirs may be formulated with sweetening agents such as glycerol, propylene glycol, sorbitol, aspartame or sucrose, and may also contain a demulcent, preservative, flavouring and/or colouring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Suppository formulations may be prepared by mixing the active ingredient with a suitable non-irritating excipient which is solid at ordinary temperatures but liquid at the rectal temperature and will therefore melt in the rectum to release the drug. Suitable excipients include, for example, cocoa butter and polyethylene glycols.

Topical formulations, such as creams, ointments, gels and aqueous or oily solutions or suspensions, may generally be obtained by formulating an active ingredient with a conventional, topically acceptable, vehicle or diluent using conventional procedure well known in the art.

Compositions for administration by insufflation may be in the form of a finely divided powder containing particles of average diameter of, for example, 30μ or much less, the powder itself comprising either active ingredient alone or diluted with one or more physiologically acceptable carriers such as lactose. The powder for insufflation is then conveniently retained in a capsule containing, for example, 1 to 50 mg of active ingredient for use with a turbo-inhaler device, such as is used for insufflation of the known agent sodium cromoglycate.

Compositions for administration by inhalation may be in the form of a conventional pressurised aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on Formulation the reader is referred to Chapter 25.2 in Volume 5 of Comprehensive Medicinal Chemistry (Corwin Hansch; Chairman of Editorial Board), Pergamon Press 1990.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

The size of the dose for therapeutic or prophylactic purposes of a compound of the Formula I will naturally vary according to the nature and severity of the conditions, the age and sex of the animal or patient and the route of administration, according to well known principles of medicine. As mentioned above, compounds of the Formula I are useful in treating diseases or medical conditions which are due alone or in part to the effects of farnesylation of ras.

In using a compound of the Formula I for therapeutic or prophylactic purposes it will generally be administered so that a daily dose in the range, for example, 0.5 mg to 75 mg per kg body weight is received, given if required in divided doses. In general lower doses will be administered when a parenteral route is employed. Thus, for example, for intravenous administration, a dose in the range, for example, 0.5 mg to 30 mg per kg body weight will generally be used. Similarly, for administration by inhalation, a dose in the range, for example, 0.5 mg to 25 mg per kg body weight will be used. Oral administration is however preferred.

Compounds of this invention may be useful in combination with known anti-cancer and cytotoxic agents. If formulated as a fixed dose such combination products employ the compounds of this invention within the dosage range described herein and the other pharmaceutically active agent within its approved dosage range. Sequential use is contemplated when a combination formulation is inappropriate.

Although the compounds of the Formula I are primarily of value as therapeutic agents for use in warm-blooded animals (including man), they are also useful whenever it is required to inhibit the effects of activation of ras by farnesylation. Thus, they are useful as pharmacological standards for use in the development of new biological tests and in the search for new pharmacological agents.

According to another aspect of the present invention there is provided individual compounds produced as end products in the Examples set out below and salts thereof.

A compound of the invention, or a salt thereof, may be prepared by any process known to be applicable to the preparation of such-compounds or structurally related compounds. Such processes are illustrated by the following representative schemes in which variable groups have any of the meanings defined for Formula I unless stated otherwise. Functional groups may be protected and deprotected using conventional methods. For examples of protecting groups such as amino and carboxylic acid protecting groups (as well as means of formation and eventual deprotection), see T. W. Greene and P. G. M. Wuts, "Protective Groups in Organic Synthesis", Second Edition, John Wiley & Sons, New York, 1991. Note abbreviations used have been listed immediately before the Examples below.

Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Specific examples of protecting groups are given below for the sake of convenience, in which "lower" signifies that the group to which it is applied preferably has 1–4 carbon atoms. It will be understood that these examples are not exhaustive. Where specific examples of methods for the removal of protecting groups are given below these are similarly not exhaustive. The use of protecting groups and methods of deprotection not specifically mentioned is of course within the scope of the invention.

A carboxy protecting group may be the residue of an ester-forming aliphatic or araliphatic alcohol or of an ester-forming silanol (the said alcohol or silanol preferably containing 1–20 carbon atoms).

Examples of carboxy protecting groups include straight or branched chain (1–12C)alkyl groups (e.g. isopropyl, t-butyl); lower alkoxy lower alkyl groups (e.g. methoxymethyl, ethoxymethyl, isobutoxymethyl; lower aliphatic acyloxy lower alkyl groups, (e.g. acetoxymethyl, propionyloxymethyl, butyryloxymethyl, pivaloyloxymethyl); lower alkoxycarbonyloxy lower alkyl groups (e.g. 1-methoxycarbonyloxyethyl, 1-ethoxycarbonyloxyethyl); aryl lower alkyl groups (e.g. p-methoxybenzyl, o-nitrobenzyl, p-nitrobenzyl, benzhydryl and phthalidyl); tri(lower alkyl)silyl groups (e.g. trimethylsilyl and t-butyldimethylsilyl); tri(lower alkyl)silyl lower alkyl groups (e.g. trimethylsilylethyl); and (2–6C)alkenyl groups (e.g. allyl and vinylethyl).

Methods particularly appropriate for the removal of carboxyl protecting groups include for example acid-, metal- or enzymically-catalysed hydrolysis.

Examples of hydroxy protecting groups include lower alkenyl groups (e.g. allyl); lower alkanoyl groups (e.g. acetyl); lower alkoxycarbonyl groups (e.g. t-butoxycarbonyl); lower alkenyloxycarbonyl groups (e.g. allyloxycarbonyl); aryl lower alkoxycarbonyl groups (e.g. benzoyloxycarbonyl, p-methoxybenzyloxycarbonyl, o-nitrobenzyloxycarbonyl, p-nitrobenzyloxycarbonyl); tri lower alkyl/arylsilyl groups (e.g. trimethylsilyl, t-butyldimethylsilyl, t-butyldiphenylsilyl); aryl lower alkyl groups (e.g. benzyl) groups; and triaryl lower alkyl groups (e.g. triphenylmethyl).

Examples of amino protecting groups include formyl, aralkyl groups (e.g. benzyl and substituted benzyl, e.g. p-methoxybenzyl, nitrobenzyl and 2,4-dimethoxybenzyl, and triphenylmethyl); di-p-anisylmethyl and furylmethyl groups; lower alkoxycarbonyl (e.g. t-butoxycarbonyl); lower alkenyloxycarbonyl (e.g. allyloxycarbonyl); aryl lower alkoxycarbonyl groups (e.g. benzyloxycarbonyl, p-methoxybenzyloxycarbonyl, o-nitrobenzyloxycarbonyl, p-nitrobenzyloxycarbonyl; trialkylsilyl (e.g. trimethylsilyl and t-butyldimethylsilyl); alkylidene (e.g. methylidene); benzylidene and substituted benzylidene groups.

Methods appropriate for removal of hydroxy and amino protecting groups include, for example, acid-, base, metal- or enzymically-catalysed hydrolysis, or photolytically for groups such as o-nitrobenzyloxycarbonyl, or with fluoride ions for silyl groups.

Examples of protecting groups for amide groups include aralkoxymethyl (e.g. benzyloxymethyl and substituted benzyloxymethyl); alkoxymethyl (e.g. methoxymethyl and trimethylsilylethoxymethyl); tri alkyl/arylsilyl (e.g. trimethylsilyl, t-butyldimethylsily, t-butyldiphenylsilyl); tri alkyl/arylsilyloxymethyl (e.g. t-butyldimethylsilyloxymethyl, t-butyldiphenylsilyloxymethyl); 4-alkoxyphenyl (e.g. 4-methoxyphenyl); 2,4-di(alkoxy)phenyl (e.g. 2,4-dimethoxyphenyl); 4-alkoxybenzyl (e.g. 4-methoxybenzyl); 2,4-di(alkoxy)benzyl (e.g. 2,4-di(methoxy)benzyl); and alk-1-enyl (e.g. allyl, but-1-enyl and substituted vinyl e.g. 2-phenylvinyl).

Aralkoxymethyl, groups may be introduced onto the amide group by reacting the latter group with the appropriate aralkoxymethyl chloride, and removed by catalytic hydrogenation. Alkoxymethyl, tri alkyl/arylsilyl and tri alkyl/silyloxymethyl groups may be introduced by reacting the amide with the appropriate chloride and removing with acid; or in the case of the silyl containing groups, fluoride ions. The alkoxyphenyl and alkoxybenzyl groups are conveniently introduced by arylation or alkylation with an appropriate halide and removed by oxidation with ceric ammonium nitrate. Finally alk-1-enyl groups may be introduced by reacting the amide with the appropriate aldehyde and removed with acid.

The invention also provides a process for preparing a compound of formula (I) as defined above which process The invention also provides a process for preparing a compound of formula (I) as defined above which process comprises reacting a compound of formula (II):

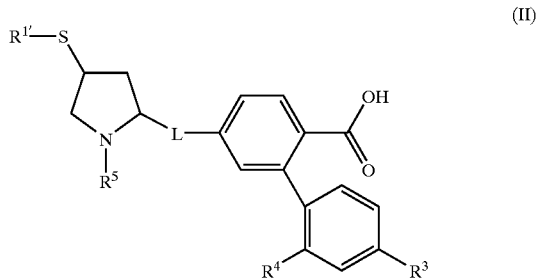

(II)

where L, $R^3$ and $R^4$ are as defined in relation to formula (I), $R^{1'}$ is a group $R^1$ as defined in relation to formula (I) or a precursor thereof, and $R^5$ is a protecting group such as BOC or ALLOC with a compound of formula (III):

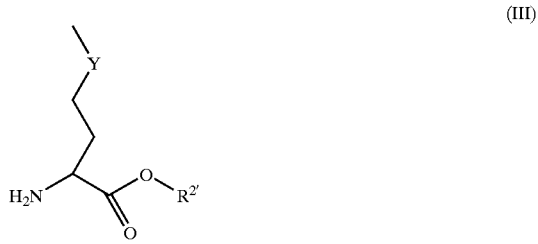

(III)

where Y is as defined in relation to formula (I) and $R^{2'}$ is a group $R^2$ as defined in relation to formula (I) or a precursor thereof;

and thereafter if desired or necessary, carrying out one or more of the following steps:
a) removing protecting groups $R^5$;
a) converting any precursor groups $R^{1'}$ and $R^{2'}$ to groups $R^1$ and $R^2$; and
b) changing said groups to different $R^1$, $R^2$ groups.

The reaction between compounds of formula (II) and (III) is suitably effected in an organic solvent such as dichloromethane in the presence of a base such as DMAP and EDC. Moderate temperatures for example of from 0 to 50° C., conveniently ambient temperature, are employed.

Precursor groups $R^{1'}$ and $R^{2'}$ may include protecting groups such as esters, which are not pharmaceutically acceptable. These may be converted to hydrogen or other prodrug groups using conventional methods as illustrated below.

Removal of protecting groups $R^5$ can be carried out using conventional methods such as reaction with TFA and/or triethylsilane.

Compounds of formula (II) are suitably prepared by deprotecting a compound of formula (IV):

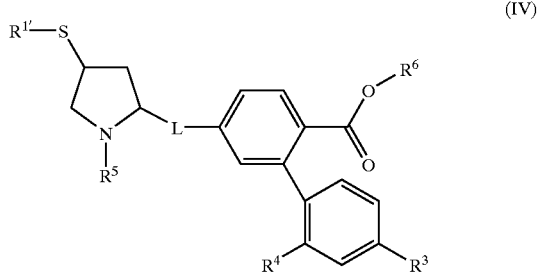

(IV)

where $R^{1'}$, $R^3$, $R^4$, $R^5$ and L are as defined in relation to formula (II) and $R^6$ is a protecting group, in particular an alkyl group such as methyl. Deprotection is suitably effected using a strong base such as an alkali metal hydroxide, in particular sodium hydroxide. The reaction is suitably effected in a solvent such as aqueous alcohol and in particular aqueous methanol, at elevated temperatures, conveniently at the reflux temperature of the solvent.

Compounds of formula (IV) where L is —CH$_2$NH— may be prepared by coupling a compound of formula (V):

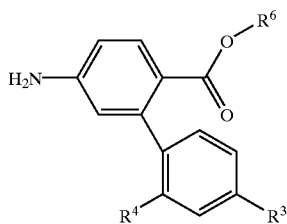

(V)

where $R^3$, $R^4$ and $R^6$ are as defined above; with an aldehyde of formula (VI):

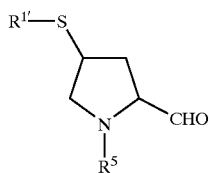

(VI)

where $R^{1'}$ and $R^5$ are as defined above.

Suitable coupling conditions include the use of a reducing agent (e.g. NaCNBH$_3$, BH$_3$, hydrogen plus catalyst, LiHBEt$_3$, di-isobutyl-aluminiumhydride, lithium aluminium hydride, sodium borohydride) in the presence of a suitable solvent e.g.methanol or ethanol & acetic acid.

Aldehydes of formula (VI) may be prepared by reduction of the compounds of formula (VII):

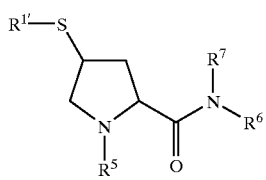

(VII)

where $R^{1'}$ and $R^5$ are as defined above and $R^6$ is alkyl such as methyl and $R^7$ is alkoxy such as methoxy.

Suitably powerful reducing agents such as lithium aluminium hydride are employed. The reaction is carried out in a solvent such as tetrahydrofuran at low temperatures, for example from –50 to 0° C., in particular at about –20° C.

Compounds of formula (VII) are suitably prepared by reacting a compound of formula (VIII):

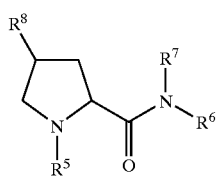

(VIII)

where $R^4$ is a leaving group such a methansulphonyloxy group, which a compound of formula (IX):

(IX)

where $R^{1'}$ is as defined above and in particular is a triphenylmethyl or trityl group. Reaction conditions would be apparent to the skilled person, but in general, the reaction is effected in an organic solvent such as dimethylformamide (DMF) at moderate temperatures, for example of from 0 to 60° C. and preferably at about 40° C.

Compounds of formula (VIII) may be prepared by reacting compounds of formula (X):

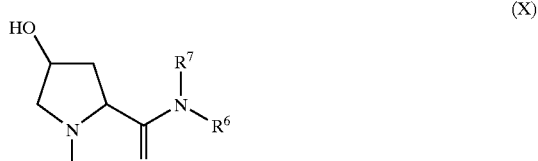

(X)

where $R^5$, $R^6$ and $R^7$ are as defined above, with a compound of formula (XI)

(XI)

where $R^8$ is as defined above and Z is a leaving group such as halogen, in particular chlorine. The reaction is suitably effected in an organic solvent such as dichloromethane in the presence of a weak base such as triethylamine. Moderate to low temperatures, for example, from –10 to 0° C. are suitably employed.

Compounds of formula (X) are suitably prepared by reacting a compound of formula (XII):

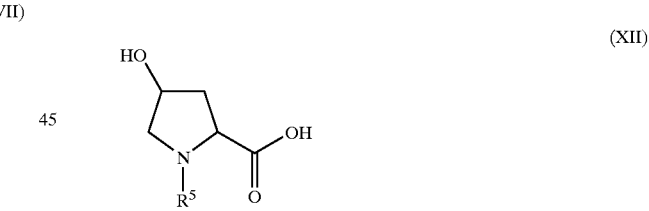

(XII)

where $R^5$ is as defined above, with a compound of formula (XIII):

(XIII)

where $R^6$ and $R^7$ are as defined above. A particular example of a compound of formula (XII) is N,O-dimethylhydroxylamine. The reaction is suitably effected in the presence of a base (such as DCCI and DMAP) and in an organic solvent such as dichloromethane.

Compounds of formula (XII) may be prepared by N-protection of the corresponding hydroxy proline derivative using known methods.

Compounds of formula (V) are suitably prepared by hydrogenation of a compound of formula (XIV):

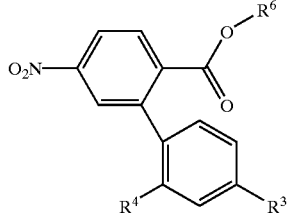
(XIV)

where $R^3$, $R^4$ and $R^6$ are as defined above. Hydrogenation is suitably effected in the presence of a catalyst such as a palladium catalyst.

Compounds of formula (XIV) are suitably prepared by reacting a compound of formula (XV):

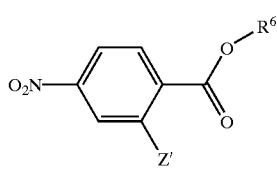
(XV)

where $R^6$ is as defined above and Z' is a leaving group such as halogen and in particular bromine, with a compound of formula (XVI):

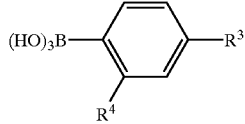
(XVI)

where $R^3$ and $R^4$ are as defined above. The reaction is suitably effected in the presence of a reagent such as ceasium fluoride, and a catalyst such as a palladium catalyst (e.g. tetrakis(triphenylphsophine) palladium(0). A suitable solvent for the reaction is dimethoxyethane and the reaction can be effected under reflux conditions.

Compounds of formula (IV) where L represents —CH$_2$O— may be prepared by reacting a compound of formula (XVII):

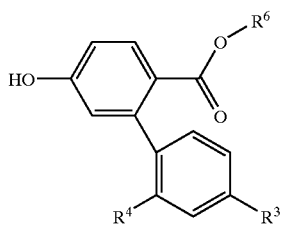
(XVII)

where $R^3$, $R^4$ and $R^6$ are as defined above, with a compound of formula (XVIII):

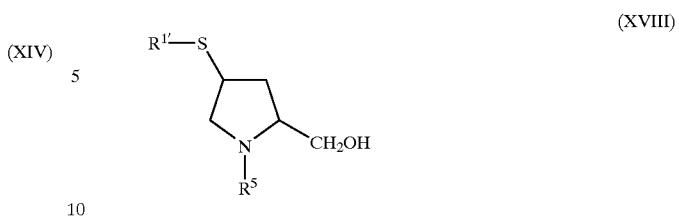
(XVIII)

where $R^{1'}$ and $R^5$ are as defined above. The reaction is suitably effected under conditions similar to those described above for the reaction between compounds of formulae (V) and (VI).

Compounds of formula (XVIII) are suitably prepared by reduction of a compound of formula (VI), for example using a reducing agent such as lithium aluminium hydride. Reduction is carried out under conventional conditions in a solvent such as tetrahydrofuran.

Compounds of formula (XVII) may be prepared by protection of the corresponding carboxylic acid, for example by esterifying the acid using an alcohol, in particular an alkyl alcohol such as methanol. The reaction is suitably effected in the presence of sulphuryl chloride or the like, at elevated temperatures, conveniently at the reflux temperature of the solvent.

The acid itself may be prepared by deprotection of a compound of formula (XIX):

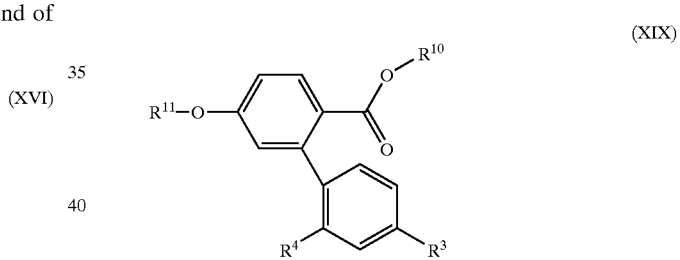
(XIX)

where $R^3$ and $R^4$ are as defined above and $R^{10}$ and $R^{11}$ are protecting groups such as alkyl, and in particular methyl groups. Suitable deprotection conditions include heating the compound with a suitable reagent such as pyridine hydrochloride to high temperatures such, for example from 200 to 250° C., and preferably at about 220° C.

Compounds of formula (XIX) are obtained by reaction of a compound of formula (XX):

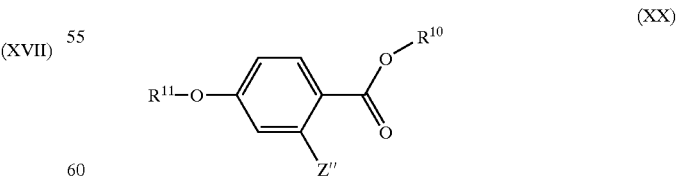
(XX)

where $R^{10}$ and $R^{11}$ are as described above and Z" is a leaving group such as halogen, in particular bromine, with a compound of formula (XVI) as defined above, using conditions similar to those described for the reaction of a compound of formula (XV) with a compound of formula (XVI).

Compounds of formula (IV) where L is —CH=CH— are suitably prepared by reacting a compound of formula (VI) as defined above with a compound of formula (XXI):

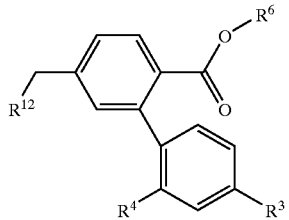

(XXI)

where $R^3$, $R^4$ and $R^6$ are as defined above and $R^{12}$ is a phosphate ion such as diethylphosphate, or a triphenylphosphine group. The reaction is a Wittig reaction and is suitably carried out under conventional conditions. Suitable reaction conditions include the use of a base (e.g. potassium carbonate, metal hydride, metal alkoxide) in the presence of an organic solvent (e.g. THF, toluene, DMSO) optionally in the presence of an aqueous solvent (2-phase system) and optionally in the presence of a catalyst complexing agent which solubilises alkali metal ions in non-polar solvents such as 1,4,7,10,13-pentaoxacyclopentadecane (also called 15-Crown-5) or 1,4,7,10,13,16-hexaoxacyclooctadecane (also called 18-Crown-6).

Compounds of formula (XXI) are suitably obtained by reacting a compound of formula (XXII):

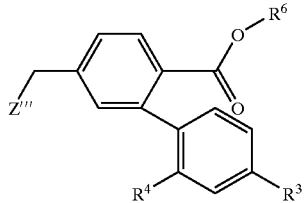

(XXII)

where $R^3$, $R^4$ and $R^6$ are as defined above and $Z'''$ is a leaving group such as halogen, and in particular bromine, with a phosphite such as triethyl phosphite. Reflux conditions are suitably employed and an inert atmosphere may be provided.

Compounds of formula (XXI) may be produced using methods described for example in PCT/GB98/00230. Preparation details are summarised further in Scheme 2 hereinafter.

If necessary or required, groups $R^1$ and $R^2$ may be changed for different such groups after any of the above preparation methods using conventional chemistry and examples of this are provided hereinafter.

Biological activity was tested as follows. Farnesyl protein transferase (FPT) was partially purified from human placenta by ammonium sulphate fractionation followed by a single Q-Sepharose® (Pharmacia, Inc) anion exchange chromatography essentially as described by Ray and Lopez-Belmonte (Ray K P and Lopez-Belmonte J (1992) Biochemical Society Transations 20 494–497). The substrate for FPT was Kras (CVIM C-terminal sequence). The cDNA for oncogenic val12 variant of human c-Ki-ras-2 4B was obtained from the plasmid pSW11-1 (ATCC). This was then subcloned into the polylinker of a suitable expression vector e.g. pIC147. The Kras was obtained after expression in the *E. coli* strain, BL21. The expression and purification of c-KI-ras-2 4B and the val12 variant in *E. coli* has also been reported by Lowe et al (Lowe P N et al. J. Biol. Chem. (1991) 266 1672–1678).

Incubations with enzyme contained 300 nM tritiated farnesyl pyrophosphate (DuPont/New England Nuclear), 120 nM ras-CVIM, 50 mM Tris HCl pH 8.0, 5 mM MgCl$_2$, 10 $\mu$M ZnCl$_2$, 5 mM dithiotheitol and compounds were added at appropriate concentrations in DMSO (3% final concentration in test and vehicle control). Incubations were for 20 minutes at 37° and were stopped with acid ethanol as described by Pompliano et al. (Pompliano D L et al (1992) 31 3800–3807). Precipitated protein was then collected onto glass fibre filter mats (B) using a Tomtec® cell harvester and tritiated label was measured in a Wallac® 1204 Betaplate scintillation counter.

Although the pharmacological properties of the compounds of the Formula I vary with structural change as expected, in general compounds of the Formula I possess an $IC_{50}$ in the above test in the range, for example, 0.01 to 200 $\mu$M.

The invention will now be illustrated in the following non-limiting Examples in which, unless otherwise stated:

(i) evaporations were carried out by rotary evaporation in vacuo and work-up procedures were carried out after removal of residual solids by filtration;

(ii) operations were carried out at room temperature, that is in the range 18–25° C. and under an atmosphere of an inert gas such as argon;

(iii) column chromatography (by the flash procedure) and medium pressure liquid chromatography (MPLC) were performed on Merck Kieselgel silica (Art. 9385) or Merck Lichroprep RP-18 (Art. 9303) reversed-phase silica obtained from E. Merck, Darmstadt, Germany;

(iv) yields are given for illustration only and are not necessarily the maximum attainable;

(v) the end-products of the Formula I have satisfactory microanalyses and their structures were confirmed by nuclear magnetic resonance (NMR) and mass spectral techniques; chemical shift values were measured on the delta scale; the following abbreviations have been used: s, singlet; d, doublet; t or tr, triplet; m, multiplet; br, broad;

(vi) intermediates were not generally fully characterised and purity was assessed by thin layer chromatographic, infra-red (IR) or NMR analysis;

(vii) melting points are uncorrected and were determined using a Mettler SP62 automatic melting point apparatus or an oil-bath apparatus; melting points for the end-products of the Formula I were determined after crystallisation from a conventional organic solvent such as ethanol, methanol, acetone, ether or hexane, alone or in admixture; and (viii) the following abbreviations have been used:

| | |
|---|---|
| ALLOC | allyloxycarbonyl |
| BOC | tert-butoxycarbonyl |
| DCCI | 1,3-dicyclohexylcarbodiimide |
| DMA | N,N-dimethylacetamide |
| DMAP | 4-dimethyl-aminopyridine |
| DMF | N,N-dimethylformamide |
| DMSO | dimethylsulfoxide |
| EDC | 1-(3-dimethylaminopropyl)-3-ethyl-carbodiimide |
| EEDQ | 2-ethoxy-1-ethoxycarbonyl-1,2-dihydroquinoline |
| HOBT | 1-hydroxybenzotriazole |
| NMM | N-methylmorpholine |
| NMM-O | 4-methylmorpholine-N-oxide |

| | |
|---|---|
| TFA | trifluoroacetic acid |
| THF | tetrahydrofuran |
| TMSI | trimethylsilyliodide |
| TPAP | tetrapropylammonium perruthenate |

EXAMPLE 1
Preparation of Compound 8 in Table 1

A mixture of Compound (xi) in Scheme 1 (0.54 g.), triethylsilane (1 ml.) and TFA (60 ml.) was stirred at ambient temperature for 1 hour under a nitrogen atmosphere. The TFA was evaporated away and the residue dissolved in ethyl acetate (5 ml.). HCl in ether (1 M, 10 ml.) was added followed by more ether (50 ml.). The resulting white solid was isolated by centrifuging, further washing with ether and re-centrifuging (3 times in all). The solid was dried under high vac. to give Compound 8 as the hydrochloride salt (0.439 g.).

Compound 8:

$^1$H NMR data (DMSO $d_6$) δ 1.16 (6H, m), 1.60–1.95 (5H, m), 1.98 (3H, s), 2.05 (2H, m), 2.24 (2H, m), 2.43 (2H, m), 2.69 (3H, m), 2.78–3.02 (3H, m), 3.14 (1H, m), 3.24–3.58 (3H, m), 3.65 (1H, m), 3.80 (1H, m), 4.02 (1H, m), 4.22 (1H, m), 4.88 (1H, m), 6.54 (1H, m), 6.68 (1H, d), 7.13 (2H, t), 7.23–7.38(3H, m), 8.11 (1H, d). MS (ES+) m/z 615 (M+H)$^+$ The starting material (Compound (xi) in Scheme 1) was synthesised from Compound (v) of Scheme 1 as described below. Compound (v) of Scheme 1 had been prepared as described in Example 1 of PCT/GB99/000369.:

A mixture of Compound (v) (9.32 g.), Compound (vi) (15 g.) of Scheme 1 and 3A powdered molecular sieves (20 g.) in methanol (250 ml.) was stirred at ambient temperature under a nitrogen atmosphere for 4 hours. Acetic acid (9.1 ml.) was then added followed by sodium cyanoborohydride (3.99 g.). The mixture was then stirred for a further 18 hours. The molecular sieves were filtered off and washed with more methanol and dichloromethane. The filtrate and washings were evaporated to dryness and the residue partitioned between sat. aqueous sodium bicarbonate solution and dichloromethane. The organic solution was dried and evaporated to dryness. The residue was purified by flash column chromatography using ethyl acetate/iso-hexane (20:80, 30:70) as eluant to give Compound (vii) of Scheme 1 (14 g.) as a white foam.

Compound (vii) of Scheme 1:

$^1$H NMR data (CDCl$_3$) δ 1.37 (9H, s), 1.38 (1H, m), 1.50 (1H, m), 2.20–2.95 (3H, m), 3.20 (2H, m), 3.60 (3H, s), 3.95 (1H, m), 5.60 (1H, m), 6.34 (1H, m), 6.51 (1H, m), 7.02 (2H, t), 7.14–7.37 (9H, m), 7.43 (8H, m), 7.80(1H, d). MS (ES+) m/z 519.46 (M+H)$^+$ A mixture of Compound (vii) (14 g.), sodium hydroxide (8 g.), water (100 ml.) and methanol (500 ml) was stirred at reflux for 18 hours. The reaction mixture was reduced in volume to 100 ml, diluted with water (100 ml.), acidified to pH 5 with aqueous citric acid (1M) and extracted with dichloromethane (2×150 ml). The combined organics were dried and evaporated to dryness to yield the desired acid, Compound (viii) in Scheme 1 as a white foam (12 g.).

Compound (viii) of Scheme 1

$^1$H NMR data (CDCl$_3$) δ 1.34 (1H, m), 1.36 (9H, s), 1.50 (1H, m), 2.15–3.00 (3H, m), 3.20 (2H, m), 3.96 (1H, m), 5.62 (1H, m), 6.32 (1H, m), 6.50 (1H, m), 7.00 (2H, t), 7.14–7.24 (9H, m), 7.45 (8H, m), 7.88 (1H, d).

A mixture of Compound (viii) (8 g.), L-methionine iso-propyl ester hydrochloride (3.2 g.), DMAP (7.1 g.) and EDC (2.9 g.) in dichloromethane (100 ml.) was stirred at ambient temperature for 18 hours. The solution was washed with aqueous citric acid (1M), brine and dried. It was then diluted with the same amount of iso-hexane and applied directly to a silica flash column eluting with ethyl acetate/iso-hexane (20:80,30:70) to give Compound (ix) (8.4 g.) as a solid white foam.

Compound (ix) of Scheme 1

$^1$H NMR data (DMSO $d_6$) δ 1.06 (6H, m), 1.26 (9H, s), 1.30 (1H, m), 1.62–1.93 (3H, m), 1.98 (3H, s), 2.11–2.32 (2H, m), 2.35–3.8 (3H, m), 2.94–3.50 (2H, m), 3.75 (1H, m), 4.20 (1H, m), 4.88 (1H, m), 6.20 (1H, m), 6.52 (1H, m), 6.60 (1H, d), 7.10 (2H, t), 7.16–7.41 (18H, m), 8.04 (1H, d).

TFA (11.3 ml.) was added to a rapidly stirring solution of Compound (ix) (8.4 g.) and triethylsilane (15.6 ml.) in dichloromethane (450 ml.) under a nitrogen atmosphere. The solution was then stirred at ambient temperature for 4 hours, basified with sat. sodium bicarbonate solution and the dichloromethane layer separated. After drying and evaporation to a smaller volume (50 ml.) it was applied directly to a silica flash column and eluted with ethyl acetate/iso-hexane (20:80,50:50) to give Compound (x) of Scheme 1(4.8 g.) as a white solid.

Compound (x) of Scheme 1:

$^1$H NMR data (CDCl$_3$) δ 1.20 (6H, m), 1.38 (1H, d), 1.45 (9H, s), 1.50–1.83 (3H, m), 1.92 (1H, m), 2.04 (3H, s), 2.20 (2H, t), 2.60 (1H, m), 3.06 (1H, m), 3.18–3.34 (2H, m), 4.02 (1H, m), 4.20 (1H, m), 4.56 (1H, m), 4.95(1H, m), 5.49(1H, m), 5.80(1H, 6.61(1H, d), 7.1(2H, t), 7.35(2H, m), 7.6(1H, d). MS (ES+) m/z 620.59 (M+H)$^+$ A mixture of Compound (x) of Scheme 1 (500 mg.), N-methylpiperidine-4-carboxylic acid (218 mg), N-methylmorpholine (409 mg), EDC (232 mg) and HOBT (109 mg) in dichloromethane (100 ml.) was stirred at ambient temperature under a nitrogen atmosphere for 18 hours. It was then applied directly to a silica flash column and eluted with ethyl acetate/iso-hexane (1:1), ethyl acetate, methanol/ethyl acetate (10:90,20:80) to give Compound (xi) in Scheme 1 (540 mg.) as a white foam.

Compound (xi) in Scheme 1:

$^1$H NMR data (DMSO $d_6$) δ 1.56 (6H, m), 1.38 (9H, s), 1.58 (2H, m), 1.70–1.97 (6H, m), 1.99 (3H, s), 2.11 (3H, s), 2.25 (2H, m), 2.45 (2H, m), 2.72 (2H, m), 2.95–3.20 (2H, m), 3.28(1H, m), 3.50 (1H, m), 3.70–4.07 (3H, m), 4.21 (1H, m), 4.88(1H, m), 6.47–6.70(2H, m), 7.11(2H, t), 7.23(1H, d), 7.3(2H, m ), 8.06(1H, d). MS (ES+) m/z 745 (M+H)$^+$

EXAMPLE 2
Preparation of Compound 9 in Table 1

Compound 9 was synthesised from Compound (xxii) in Scheme 2 using a method analogous to that described in Example 1.

Compound 9

$^1$H NMR data (DMSO $d_6$) δ 1.90 (2H, m), 1.98 (3H, s), 1.99 (3H, s), 2.01–2.28 (2H, m), 2.70 (3H, m), 3.02 (2H, m), 3.33 (2H, m), 3.68 (1H, m), 3.93 (2H, m), 4.38 (4H, m), 4.81 (1H, m), 4.98 (1, m), 6.58 (1H, dd), 6.90 (1H, d), 7.20 (2H, m), 7.40 (2H, m), 7.46 (1H, m), 7.54 (1H, m), 7.62 (1H, dd), 8.24 (1H, m), 8.66 (1H, dd), 8.83 (1H, m), 9.06 (1H, d). MS (ES+) m/z 677 (M+H)$^+$ The starting material (compound (xxii)) was synthesised from Compound (xvi) in Scheme 2 as described hereinafter. The preparation of Compound (xvi) is given as Example 14 of PCT/GB98/00230.

Compound (xvi) (20 g) was dissolved in triethyl phosphite (110 ml) and heated to 160° C. under a nitrogen atmosphere for 18 hours. The solution was evaporated to dryness and the residue was dissolved in dichloromethane and applied directly to a silica flash column and eluted with ethyl acetate/iso-hexane (50:50) and ethyl acetate to give Compound (xvii) as a colourless oil (20.7 g).

Compound (xvii) in Scheme 2:

$^1$H NMR data (DMSO d$_6$) δ 1.16 (6H, t), 3.34 (2H, d), 3.58 (3H, s), 3.94 (4H, m), 7.19–7.34 (5H, m), 7.39 (1H, m), 7.71 (1H, d). MS (ES+) m/z 381.3 (M+H)$^+$ Compound (xvii) (18.0 g) was dissolved in tetrahydrofuran (500 ml) and cooled to −30° C. Potassium tert-butoxide (47.3 ml of a 1.0M solution in tetrahydrofuran) was added over 10 minutes and then a solution of compound (vi) (22.4 g) in tetrahydrofuran (15 ml) was added over 8 minutes. After 10 minutes aqueous saturated ammonium chloride solution (200 ml) was added and the reaction mixture allowed to warm to ambient temperature. The organic layer was separated, the aqueous washed with ethyl acetate (100 ml) and the combined organics dried and evaporated to dryness. Purification by flash column chromatography using ethyl acetate/iso-hexane (10:90, 15:85 then 20:80) as eluant gave Compound (xviii) in Scheme 2 as a colourless foam (24 g).

Compound (xviii) in Scheme 2

$^1$H NMR data (DMSO d$_6$) δ 1.22 (3H, bs), 1.28 (1H, m), 1.60 (1H, m), 2.48–3.20 (3H, m), 3.58 (3H, s), 4.10 (1H, m), 6.23–6.45 (2H, m), 7.18–7.42 (20H, m), 7.45 (1H, d), 7.72 (1H, d). MS (ES+) m/z 699 (M+H)$^+$ Compound (xviii) was converted to compound (xxii) in Scheme 2 by the route analogous to that described in Example 1 for the preparation of Compound (xi) using the appropriate intermediates.

Compound (xix) of Scheme 2:

$^1$H NMR data (DMSO d$_6$) δ: 1.15–1.35 (10H, m), 1.52–1.65 (1H, m), 2.66–2.81 (3H, m), 4.09 (1H, m), 6.27 (1H, dd), 6.40 (1H, d), 7.15–7.39 (20H, m), 7.41 (1H, dd), 7.70 (1H, d), 12.69 (1H, s). MS (ES+) m/z 686.6 (M+H)$^+$ Compound (xx) in Scheme 2:

$^1$H NMR data (DMSO d$_6$) δ 1.22 (10H, bs), 1.57 (3H, m), 1.80 (4H, m), 1.98 (3H, s), 2.16 (3H, s), 2.18–2.28 (4H, m), 2.58 (1H, m), 2.75 (4H, m), 4.08 (1H, m), 4.30 (1H, m), 4.70 (1H, m), 6.24 (1H, dd), 6.40 (1H, d), 7.18 (2H, m), 7.21–7.47 (20H, m), 8.57 (1H, bd).

Compound (xxi) in Scheme 2

$^1$H NMR data (DMSO d$_6$) δ 1.39 (10H, bs), 1.63–1.80 (6H, m), 1.81–1.98 (3H, m), 2.02 (3H, s), 2.19 (2H, m), 2.32 (3H, s), 2.63 (3H, m), 3.20 (1H, m), 3.30 (1H, m), 4.02 (1H, m), 4.40 (1H, m), 4.62 (1H, m), 4.78 (1H, m), 5.96 (1H, d), 6.25 (1H, m), 6.50 (1H, m), 7.10 (2H, t), 7.30 (1H, s), 7.39 (3H, m), 7.63 (1H, d). MS (ES+) m/z 672 (M+H)$^+$ Compound (xxii) in Scheme 2

$^1$H NMR data (DMSO d$_6$) δ 1.43 (9H, s), 1.63–2.09 (5H, m), 2.20 (2H, m), 2.26 (3H, s), 2.27 (3H, s), 2.40 (2H, m), 2.60 (2H, m), 2.79 (1H, m), 3.42 (1H, m), 3.70 (2H, dd), 4.18 (2H, m), 4.61 (2H, m), 4.68 (1H, m), 5.98 (1H, d), 6.25 (1H, dd), 6.52 (1H, d), 7.10 (2H, t), 7.38 (4H, m), 7.62 (1H, d), 8.15 (1H, m), 8.79 (1H, dd), 9.13 (1H, dd). MS (ES+) m/z 777 (M+H)$^+$

EXAMPLE 3

Preparation of Compound 5 in Table 1

Compound 5 in Table 1 was synthesised from Compound (xxv) in Scheme 2 using a method analogous to that described in Example 1 for the preparation of Compound (8).

Compound 5:

$^1$H NMR data (DMSO d$_6$) δ: 1.16 (6H, m), 1.72–1.96 (4H, m), 1.97 (3H, s), 1.99–2.10 (2H, m), 2.11–2.29 (2H, m), 2.42 (1H, m), 2.53–2.74 (4H, m), 2.78–3.01 (2H, m), 3.10–3.20 (1H, m), 3.29–3.45 (2H, m), 3.64–3.76 (1H, m), 4.01–4.12 (1H, m), 4.22–4.40 (2H, m), 4.88 (1H, m), 6.52 (1H, dd), 6.86 (1H, d), 7.14–7.22 (2H, t), 7.36–7.47 (4H, m), 7.52 (1H, d), 8.58 (1H, d). MS (ES+) m/z 642.6 (M+H)$^+$ Compound (xxv) in Scheme 2 was synthesised from Compound (xix) by the route described in Example 2 for the preparation of Compound (xxii) using the appropriate intermediates.

Compound (xxiii) of Scheme 2:

$^1$H NMR data (DMSO d$_6$) δ: 1.10–1.19 (6H, m), 1.20–1.30 (10H, m), 1.60 (1H, m), 1.72–1.86 (2H, m), 1.96 (3H, s), 2.12–2.27 (2H, m), 2.50 (1H, m), 2.68–2.80 (2H, m), 4.04 (1H, br s), 4.26 (1H, m), 4.88 (1H, m), 6.25 (1H, dd), 6.40 (1H, d), 7.10–7.44 (22H, m), 8.53 (1H, d). MS (ES+) m/z 859.5 (M+H)$^+$ Compound (xxiv) of Scheme 2:

$^1$H NMR data (DMSO d$_6$) δ: 1.16 (6H, m), 1.21–1.41 (10H, m), 1.63–1.86 (3H, m), 1.97 (3H, s), 2.11–2.27 (2H, m), 2.45–2.59 (1H, m), 2.90 (1H, d), 3.01–3.11 (1H, t), 3.80–3.89 (1H, m), 4.21–4.34 (2H, m), 4.83–4.94 (1H, m), 6.35 (1H, dd), 6.48 (1H, d), 7.15 (2H, t), 7.34–7.48 (5H, m), 8.53 (1H, d). MS (ES+) m/z 617.6 (M+H)$^+$ Compound (xxv) of Scheme 2:

$^1$H NMR data (DMSO d$_6$) δ 1.16 (6H, m), 1.25–1.40 (9H, br s), 1.48–1.61 (2H, m), 1.71–1.91 (6H, m), 1.97 (3H, s), 2.09 (3H, s), 2.10–2.29 (2H, m), 2.39–2.47 (1H, m), 2.54–2.61 (1H, m), 2.65–2.74 (2H, m), 3.08–3.17 (1H, m), 3.28 (1H, m), 3.80–3.95 (2H, m), 4.21–4.30 (1H, m), 4.35–4.45 (1H, m), 4.88 (1H, m), 6.33 (1H, dd), 6.48 (1H, d), 7.12–7.20 (2H, t), 7.34–7.48 (5H, m), 8.54 (1H, d).

EXAMPLE 4

Preparation of Compound 4 in Table 1

To a solution of Compound (xxxvi) in Scheme 3 (2.85 g.) in dichloromethane (130 ml.), with sufficient methanol added to cause dissolution, was added water (0.183 ml.) and the solution de-gassed with nitrogen. A catalytic quantity of bis(triphenylphosphine)palladium(II) dichloride (45 mg.) was added and the pale yellow solution stirred at ambient temperature for 10 minutes before tributyltin hydride (5 ml.) was added. After 30 minutes the reaction was concentrated in vacuo (10 ml.) and the reaction mixture purified by flash column chromatography eluting with methanol/dichloromethane (10:90–30:70) to give a pale yellow foam. This was re-dissolved in ethyl acetate and HCl in ether (1M.) added. The white precipitate formed was isolated by centrifuging, washing with more ether and re-centrifuging (3 times in all) and finally drying to give Compound 4 (1.3 g.) as a pale yellow foam.

$^1$H NMR data(free base) (DMSO d$_6$) δ 1.75–1.85 (4H, m), 1.95 (3H, s), 2.15 (3H, s), 2.15–2.3 (4H, m), 2.5–2.6 (3H, m), 2.8 (1H, dd), 3.35 (2H, dd), 3.5–3.6 (2H, m), 3.85–4.05 (4H, 2×m), 4.2–4.3 (1H, m), 4.6–4.7 (1H, m), 6.9 (1H, d), 7.0 (1H, dd), 7.1–7.3 (4H, 2×m), 7.35–7.4 (3H, m), 7.45–7.55 (2H, m), 7.65–7.75 (1H, m), 7.9 (1H, d), 8.4 (1H, d). MS (ES+) m/z 680 (M+H)$^+$ The starting material (Compound (xxxvi)) was synthesised as follows.

Triethylamine (29 ml.) was added to a solution of methyl 4-methoxysalicylate (Compound xxvi in Scheme 3) (25.0 g.) in dichloromethane (500 ml.) and the solution cooled to 0° C. Trifluoromethanesulphonic anhydride (29 ml.) was added dropwise and the reaction stirred at ambient temperature for 1 hour. Additional portions of triethylamine and trifluoromethanesulphonic anhydride were added over 16 hours until HPLC showed absence of starting material. The reaction was washed with 2N hydrochloric acid and the organic phase evaporated to give a brown oil. Purification by flash chromatography (ethyl acetate/iso-hexane (50:50) gave methyl 4-methoxy-2-trifluoromethylsulphonyloxybenzoate (Compound xxvii) as a pale yellow oil (23.4 g).

$^1$H NMR data (CDCl$_3$,) δ 3.88 (3H, s), 3.93 (3H, s), 6.79 (1H, d), 6.96 (1H, dd), 8.06 (1H, d). MS (ES+) m/z 315 (M+H)$^+$ Saturated aqueous sodium hydrogen carbonate solution (50 ml) was added to a solution of methyl 4-methoxy-2-trifluoromethanesulphonylbenzoate (6.3 g.) and 4-fluorobenzeneboronic acid (3.36 g.) in DME (150 ml) at ambient temperature under an argon atmosphere. Tetrakis (triphenylphosphine) palladium (928 mg.) was added and the reaction heated and stirred at reflux for 3.5 hours resulting in a homogeneous solution. After cooling to ambient temperature, the reaction was partitioned between ethyl acetate and water. The organic phase was washed with 2N hydrochloric acid, water and brine, filtered through 1PS filter paper and the solvent removed to give methyl 4-methoxy-2-(4-fluorophenyl)benzoate as a yellow-oily solid (7.2 g) which was used without further purification.

$^1$H NMR data (CDCl$_3$,) δ 3.65 (3H, s), 3.87 (3H, s), 6.79 (1H, d), 6.91 (1H, dd), 7.08 (2H, dd), 7.25 (2H, dd), 7.90 (1H, d). MS (ES+) m/z 261 (M+H)$^+$ To a solution of methyl 4-methoxy-2-(4-fluorophenyl) benzoate (9.8 g.) in methanol (75 ml.) was added 2N aqueous sodium hydroxide solution (45 ml.) and the mixture heated at reflux for 1.5 hours. The reaction was cooled to ambient temperature, filtered and the filtrate concentrated to remove the methanol. The residual aqueous phase was washed with ether, acidified to pH 1 using concentrated hydrochloric acid and extracted with ethyl acetate. The organic extracts were dried and the solvent removed to give 4-methoxy-2-(4-fluorophenyl)benzoic acid (Compound (xxix) in Scheme 3) as a white solid (7.7 g), which was used without further purification.

$^1$H NMR data (DMSO d$_6$,) δ 3.80 (3H, s), 6.80 (1H, d), 6.98 (1H, dd), 7.18 (2H, dd), 7–31 (2H, dd), 7.76 (1H, d). MS (ES+) m/z 247 (M+H)$^+$ A solution of boron tribromide in dichloromethane (1M, 66 ml.) was added dropwise to a stirred solution of 4-methoxy-2-(4-fluorophenyl)benzoic acid (7.7 g.) in dried dichloromethane (215 ml) under an argon atmosphere at 0° C. The reaction was stirred for 1 hour at 0° C., allowed to warm to ambient temperature and stirred for 16 hours. The reaction was poured into ice water and extracted with dichloromethane followed by ethyl acetate. The combined organic extracts were washed with saturated aqueous sodium hydrogen carbonate and the aqueous phase acidified to pH 1 with concentrated hydrochloric acid and extracted with ethyl acetate. The ethyl acetate extracts were dried and evaporated to dryness to give 4-hydroxy-2-(4-fluorophenyl) benzoic acid (Compound xxx) as a yellow oil (4.5 g), which was used without further purification.

$^1$H NMR data (DMSO d$_6$,) δ 6.63 (1H, d), 6.80 (1H, dd), 7.15 (2H, dd), 7.26 (2H, dd), 7.71 (1H, d). MS (ES+) m/z 233 (M+H)$^+$ Sulphuryl chloride (44 ml.) was added to compound (xxx) (21.7 g.) in methanol (220 ml.) and the solution was refluxed and stirred for 18 hours. The methanol was evaporated away and the residue was partitioned between ethyl acetate and saturated sodium bicarbonate. The organic phase was washed with brine, filtered through phase separating paper and evaporated to dryness to give compound (xxxi) as a white solid (18.2 g.)

$^1$H NMR data (CDCl$_3$,) δ 3.65 (3H, s), 5.5 (1H, br s), 6.75 (1H, d), 6.85 (1H, dd), 7.05 (2H, dd), 7.25 (2H, dd), 7.85 (1H, d). MS (ES+) m/z 247 (M+H)$^+$ A solution of diethyl azodicarboxylate (7.44 g. in dichloromethane (50 ml.)) was added dropwise to a stirred solution of compound (xxxi) (10 g.), compound (xxxii) (14.2 g.) and triphenyl phosphine (11.21 g.) in dichloromethane (200 ml.) cooled to 0° C. under a nitrogen atmosphere. The reaction was then stirred at 0° C. for a further 30 minutes and at ambient temperature for 18 hours. The reaction mixture was reduced in volume to 60 ml. and applied directly to a silica flash column which was eluted with ethyl acetate/iso-hexane (20:80–50:50) to give compound (xxxiii) as a colourless oil (20.3 g.).

$^1$H NMR data (CDCl$_3$,) δ 1.45 (9H, s), 2.05–2.15 (1H, m), 2.55–2.7 (1H, m), 3.25–3.35 (1H, m), 3.6 (3H, s), 3.75–3.8 (1H, m), 4.05–4.2 (2H, m), 4.2–4.3 (2H, m), 4.55 (2H, d), 5.2 (1H, d), 5.3 (1H, d), 5.8–6.0 (1H, m), 6.8 (1H, m), 6.9 (1H, m), 7.05 (2H, dd), 7.25 (2H, dd), 7.9 (1H, d). MS (ES+) m/z 546 (M+H)$^+$ A mixture of compound (xxxiii) (10 g.), 2N aqueous sodium hydroxide (23 ml.), water (70 ml.) and methanol (150 ml.) was heated at reflux for 18 hours. More 2N sodium hydroxide (5 ml.) and water (30 ml.) was added and the reaction mixture heated at reflux for another 24 hours. The mixture was cooled to ambient temperature, the methanol evaporated away and the aqueous residue washed with ether and acidified to pH 2 with 2N hydrochloric acid. It was then extracted with ethyl acetate, dried and evaporated to dryness to give compound (xxxiv) as a colourless gum (7.51 g.)

$^1$H NMR data (DMSO d$_6$) δ 1.8–1.9 (1H, m), 2.5–2.6 (1H, m), 3.0–3.15 (1H, m), 3.3–3.4 (1H, m), 3.9 (1H, dd), 4.05–4.15 (1H, m), 4.2–4.3 (2H, m), 4.5 (2H, m), 5.1–5.25 (2H,m), 5.8–6.0 (1H, m), 6.8 (1H, m), 7.0 (1H, dd), 7.2 (2H, dd), 7.35 (2H, dd), 7.8 (1H, d). MS (ES+) m/z 432 (M+H)$^+$ To a solution of Compound (xxxiv) (7.5 g.) in dry dichloromethane (400 ml) under nitrogen was added triethylamine (4.84 ml.) followed by benzoyl chloride (2.12 ml.) and the reaction stirred at ambient temperature for 16hours. The reaction was quenched with 2N HCl and extracted with ethyl acetate. The combined organics were washed with brine, dried and concentrated in vacuo to give Compound (xxxv) as a pale yellow foam (9.35 g). MS (ES+) m/z 536 (M+H)$^+$ Compound (xxxv) was converted to Compound (xxxvi) using a method analogous to that described in Example 2 above for the preparation of Compound (xx).

$^1$H NMR data (CDCl$_3$) δ 1.7–1.9 (3H, m), 1.99–2.05 (2H, m), 2.05 (3H, 2×s), 2.15–2.25 (4H, m), 2.45 (3H, s), 2.6–2.85 (4H, 2×br.m), 3.4 (1H, dd), 4.1–4.45 (5H, 2×m), 4.55–4.6 (3H, m), 4.8–4.9 (1H, br.m), 5.2 (1H, d), 5.3 (1H, d), 5.9 (1H, d), 5.9–6.0 (1H, m), 6.85 (1H, m), 6.95 (1H, m), 7.1 (2H, dd), 7.35–7.5 (5H, m), 7.6 (1H, dd), 7.6 (1H, d), 7.9 (2H, d). MS (ES+) m/z 764 (M+H)$^+$

EXAMPLE 5

Pharmaceutical Compositions

The following illustrate representative pharmaceutical dosage forms of the invention as defined herein (the active ingredient being termed "Compound X"), for therapeutic or prophylactic use in humans:

| (a) Tablet I | mg/tablet |
|---|---|
| Compound X | 100 |
| Lactose Ph. Eur | 182.75 |
| Croscarmellose sodium | 12.0 |
| Maize starch paste (5% w/v paste) | 2.25 |
| Magnesium stearate | 3.0 |

| (b) Tablet II | mg/tablet |
|---|---|
| Compound X | 50 |
| Lactose Ph. Eur | 223.75 |
| Croscarmellose sodium | 6.0 |
| Maize starch | 15.0 |
| Polyvinylpyrrolidone (5% w/v paste) | 2.25 |
| Magnesium stearate | 3.0 |

| (c) | Tablet III | mg/tablet |
|---|---|---|
| | Compound X | 1.0 |
| | Lactose Ph. Eur | 93.25 |
| | Croscarmellose sodium | 4.0 |
| | Maize starch paste (5% w/v paste) | 0.75 |
| | Magnesium stearate | 1.0 |
| (d) | Capsule | mg/capsule |
| | Compound X | 10 |
| | Lactose Ph. Eur | 488.5 |
| | Magnesium | 1.5 |
| (e) | Injection I | (50 mg/ml) |
| | Compound X | 5.0% w/v |
| | 1 M Sodium hydroxide solution | 15.0% v/v |
| | 0.1 M Hydrochloric acid (to adjust pH to 7.6) | |
| | Polyethylene glycol 400 | 4.5% w/v |
| | Water for injection to 100% | |
| (f) | Injection II | (10 mg/ml) |
| | Compound X | 1.0% w/v |
| | Sodium phosphate BP | 3.6% w/v |
| | 0.1 M Sodium hydroxide solution | 15.0% v/v |
| | Water for injection to 100% | |
| (g) | Injection III | (1 mg/ml, buffered to pH 6) |
| | Compound X | 0.1% w/v |
| | Sodium phosphate BP | 2.26% w/v |
| | Citric acid | 0.38% w/v |
| | Polyethylene glycol 400 | 3.5% w/v |
| | Water for injection to 100% | |
| (h) | Aerosol I | mg/ml |
| | Compound X | 10.0 |
| | Sorbitan trioleate | 13.5 |
| | Trichlorofluoromethane | 910.0 |
| | Dichlorodifluoromethane | 490.0 |
| (i) | Aerosol II | mg/ml |
| | Compound X | 0.2 |
| | Sorbitan trioleate | 0.27 |
| | Trichlorofluoromethane | 70.0 |
| | Dichlorodifluoromethane | 280.0 |
| | Dichlorotetrafluoroethane | 1094.0 |
| (j) | Aerosol III | mg/ml |
| | Compound X | 2.5 |
| | Sorbitan trioleate | 3.38 |
| | Trichlorofluoromethane | 67.5 |
| | Dichlorodifluoromethane | 1086.0 |
| | Dichlorotetrafluoroethane | 191.6 |
| (k) | Aerosol IV | mg/ml |
| | Compound X | 2.5 |
| | Soya lecithin | 2.7 |
| | Trichlorofluoromethane | 67.5 |
| | Dichlorodifluoromethane | 1086.0 |
| | Dichlorotetrafluoroethane | 191.6 |
| (l) | Ointment | ml |
| | Compound X | 40 mg |
| | Ethanol | 300 μl |
| | Water | 300 μl |
| | 1-Dodecylazacycloheptan-2-one | 50 μl |
| | Propylene glycol | to 1 ml |

Note

The above formulations may be obtained by conventional procedures well known in the pharmaceutical art. The tablets (a)–(c) may be enteric coated by conventional means, for example to provide a coating of cellulose acetate phthalate. The aerosol formulations (h)–(k) may be used in conjunction with standard, metered dose aerosol dispensers, and the suspending agents sorbitan trioleate and soya lecithin may be replaced by an alternative suspending agent such as sorbitan monooleate, sorbitan sesquioleate, polysorbate 80, polyglycerol oleate or oleic acid.

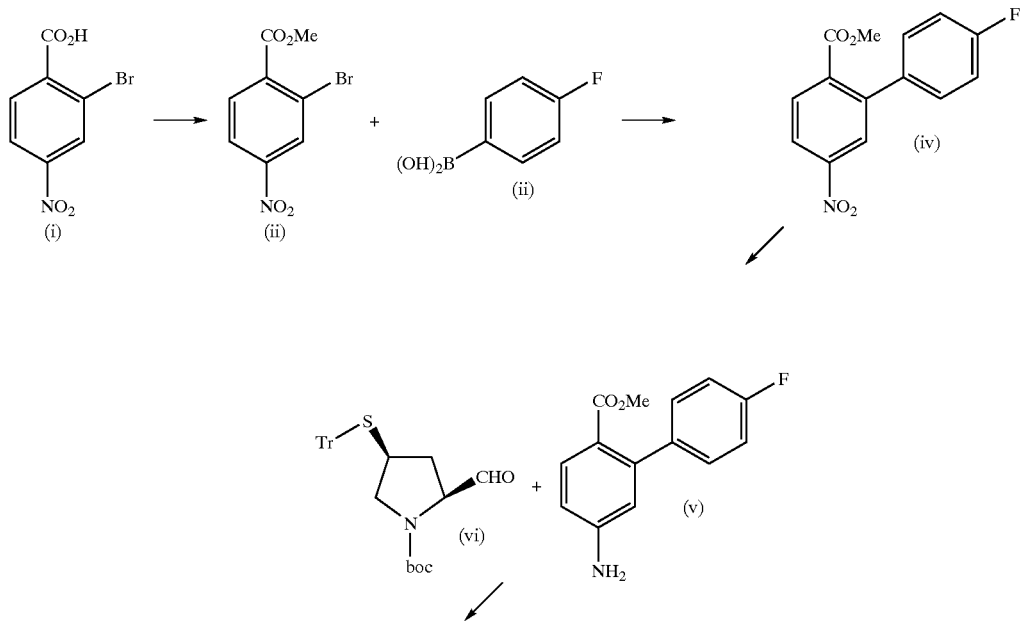

Scheme 1

27 28
-continued
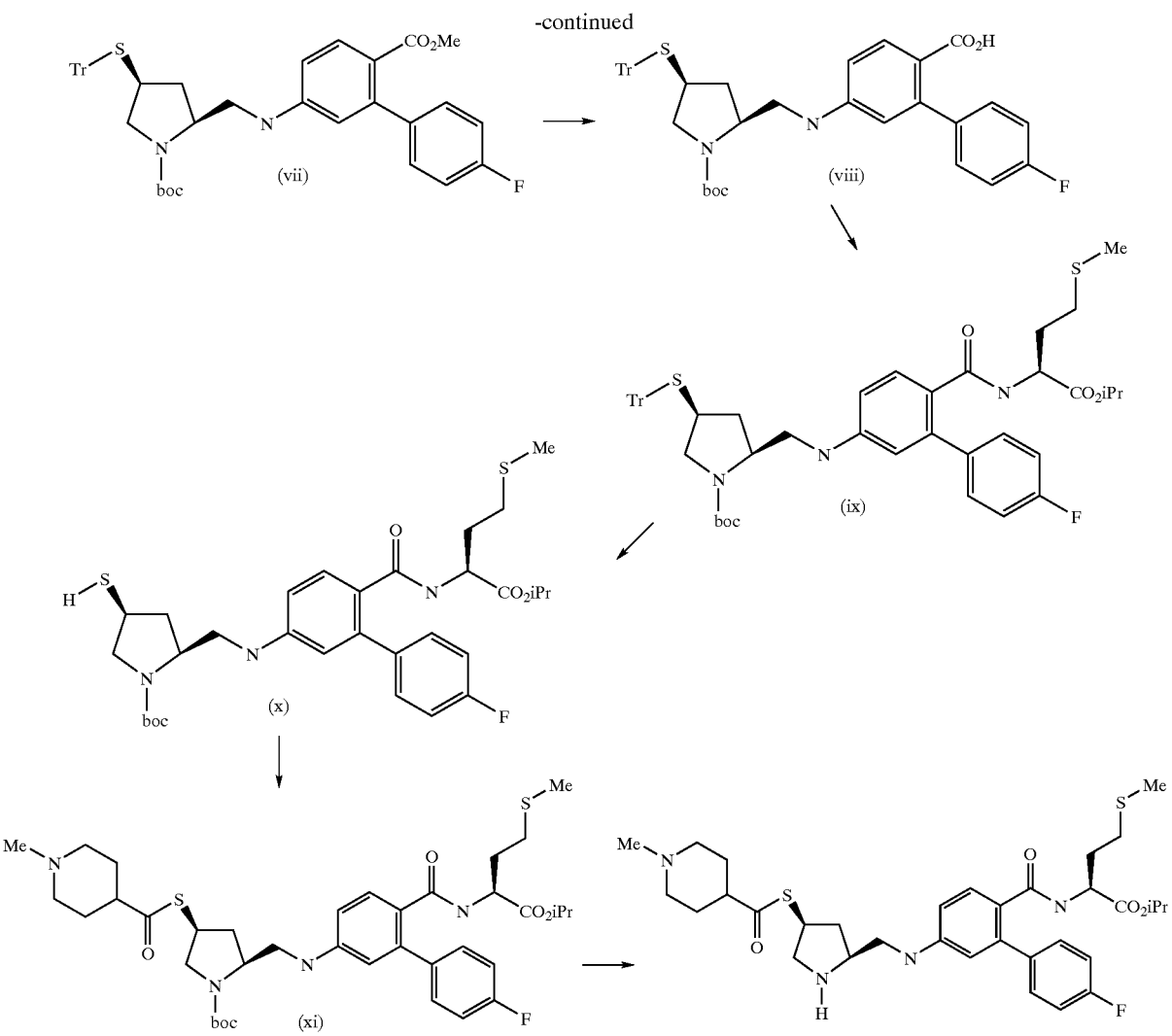
Scheme 2
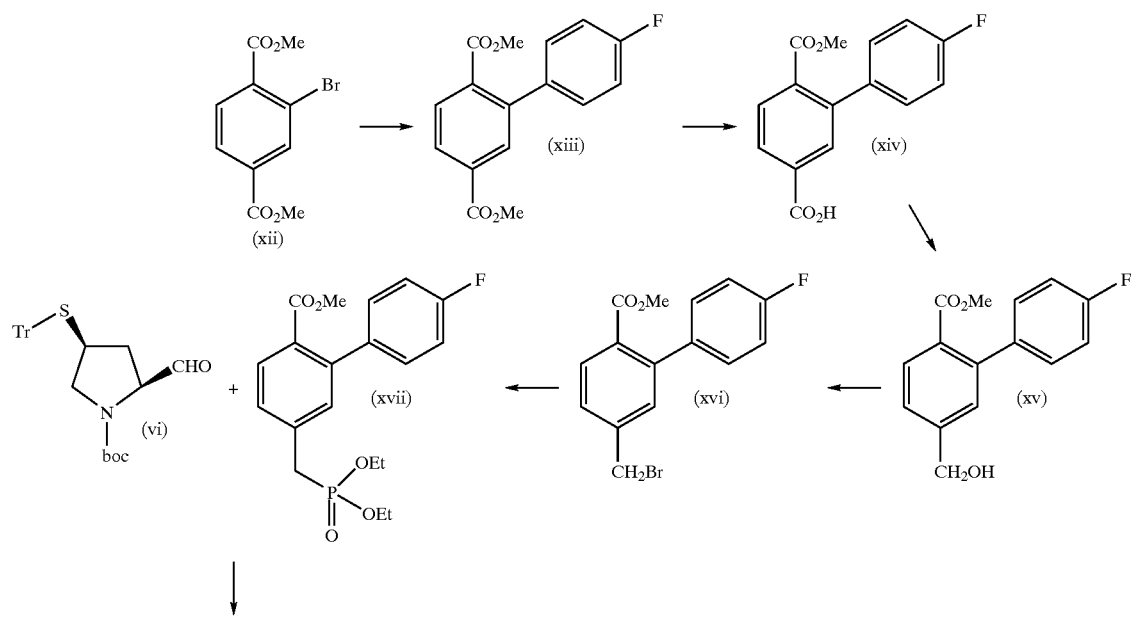

29 30
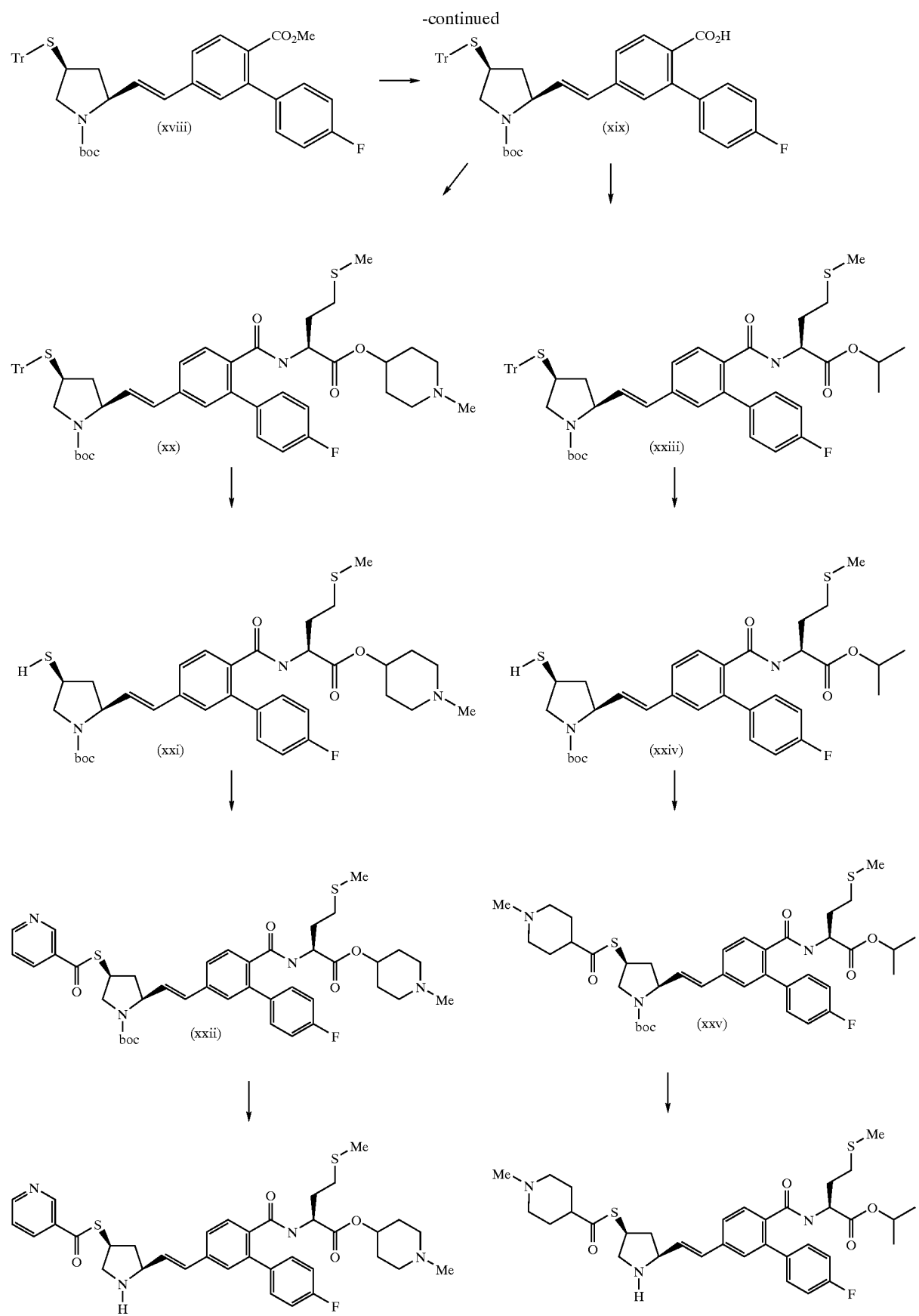
-continued

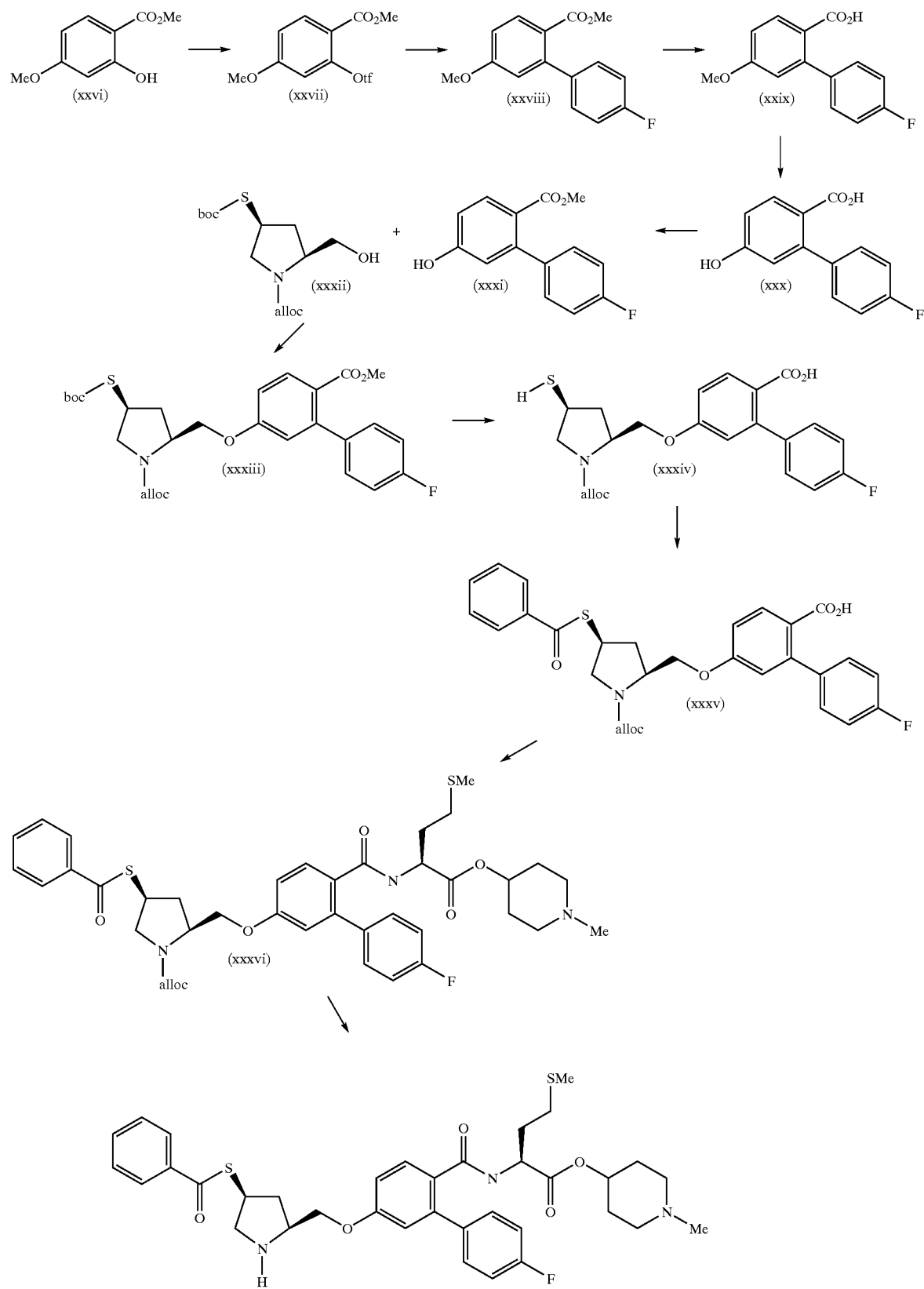

What is claimed is:

1. A compound of formula (I)

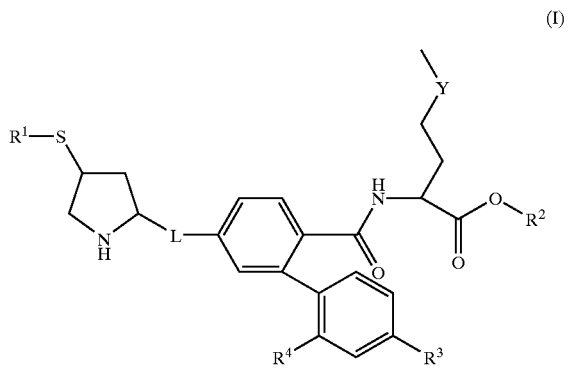

wherein:

$R^1$ and $R^2$ are independently selected from H or a prodrug moiety;

$R^3$ is hydrogen or halogen;

$R^4$ is hydrogen or halogen;

L is —CH=CH— or —CH$_2$—Z— where Z is NH or O;

Y is S, S(O) or S(O)$_2$;

or a salt thereof, provided that at least one of $R^3$ and $R^4$ is halogen.

2. A compound of formula (I) as claimed in claim 1 wherein the group $R^1$ is hydrogen or a prodrug moiety of the formula $R^5C(O)$— where $R^5$ is an optionally substituted aryl or heterocyclyl group.

3. A compound of formula (I) as claimed in claim 2 wherein $R^5$ is optionally substituted phenyl, optionally substituted pyridyl, optionally substituted furyl, optionally substituted isoxazole, optionally substituted tetrahydropyridyl or optionally substituted tetrahydrofuryl.

4. A compound of formula (I) as claimed in claim 3 wherein $R^5$ is phenyl, pyridyl or N-methylpiperidine.

5. A compound of formula (I) as claimed in claim 2 wherein $R^5$ is optionally substituted by alkyl, haloalkyl, hydroxy, alkoxy or cyano.

6. A compound of formula (I) as claimed in claim 1 wherein $R^2$ is selected from hydrogen, a $C_{1-4}$alkyl group, or an optionally substituted heterocyclic group.

7. A compound of formula (I) as claimed in claim 5 wherein $R^3$ is a halo atom.

8. A compound of formula (I) as claimed in claim 5 wherein $R^4$ is hydrogen or fluorine.

9. A compound of formula (I) as claimed in claim 5 wherein the linking group L is —CH=CH—.

10. A compound of formula (I) as claimed in claim 5 wherein the Y is S or S(O)$_2$.

11. A compound of formula (I)

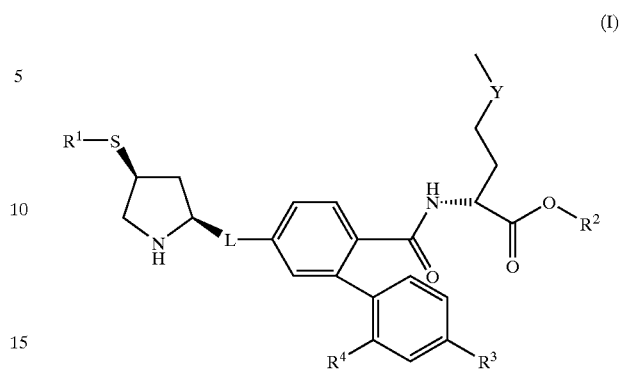

wherein:

$R^1$ and $R^2$ are independently selected from H or a prodrug moiety;

$R^3$ is hydrogen or halogen;

$R^4$ is hydrogen or halogen;

L is —CH=CH— or —CH$_2$—Z— where Z is NH or O;

Y is S, S(O) or S(O)$_2$;

or a salt thereof; privided that at least one of $R^3$ or $R^4$ is halogen.

12. A new compound of formula (Ia)

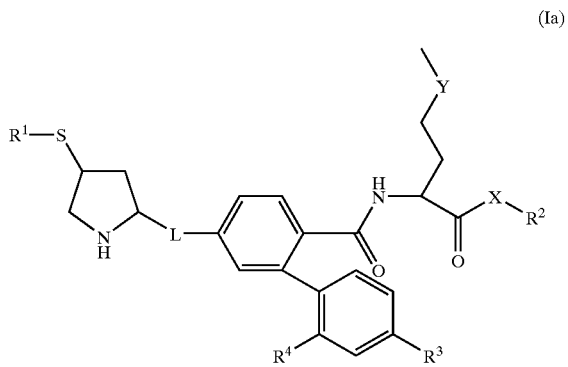

wherein:

$R^1$ and $R^2$ are independently selected from H or a prodrug moiety;

X is O or a direct bond;

$R^3$ is hydrogen or halogen;

$R^4$ is hydrogen or halogen;

L is —CH=CH— or —CH$_2$—Z— where Z is NH or O;

Y is S, S(O) or S(O)$_2$;

or a salt thereof, provided that at least one of $R^3$ and $R^4$ is halogen.

13. A compound of formula (Ia) as claimed in claim 12, wherein X is O and $R^2$, together with the carboxy group to which it is attached, forms an in vivo cleavable ester.

14. A compound of formula (Ia) as claimed in claim 12, wherein X is a direct bond and $R^2$, together with the carbonyl group to which it is attached, forms an in vivo cleavable amide.

15. A compound of formula (Ia) as claimed in claim 14 wherein $R^2$, together with the carbonyl group to which it is attached, forms a N—$C_{1-6}$ alkylamide or N,N-di-($C_{1-6}$alkyl) amide.

16. A compound of formula (Ia) as claimed in claim 13 wherein $R^2$ together with the carboxy group to which it is attached forms a $C_{1-6}$alkyl ester or $C_{1-6}$cycloalkyl ester; $C_{1-6}$alkoxymethyl ester; $C_{1-6}$alkanoyloxymethyl ester; phthalidyl ester; $C_{3-8}$cycloalkoxycarbonyloxy$C_{1-6}$alkyl ester; 1,3-dioxolan-2-ylmethyl ester; $C_{1-6}$alkoxycarbonyloxyethyl ester; aminocarbonylmethyl ester and mono- or di-N—($C_{1-6}$alkyl) versions thereof; or a pharmaceutically acceptable ester of an optionally substituted heterocyclic group.

17. A pharmaceutical composition comprising a compound as defined in any one of claims 1–5, 16, 6–11 and 12–15 together with a pharmaceutically acceptable diluent or carrier.

18. A method of treating a disease or medical condition mediated through farnesylation of ras by farnesyl transferase which comprises administering an effective farnesyl transferase inhibiting amount of a compound according to any one of claims 1 and 11.

19. The method of claim 18 wherein the disease or medical condition is a carcinoma of the bladder, breast, colon, kidney, liver, lung, ovary, pancreas, stomach, cervix, thyroid or skin.

20. The method of claim 18 wherein the disease or medical condition is a hematopoietic tumor of lymphoid lineage, selected from lymphocytic leukaemia, B-cell lymphoma and Burketts lymphoma.

21. The method of claim 18 wherein the disease or medical condition is a hematopoietic tumor of myeloid lineage, selected from acute and chronic myelogenous leukemias and promyelocytic leukaemia.

22. The method of claim 18 wherein the disease or medical condition is a tumor of mesenchymal origin, selected from fibrosarcoma and rhabdomyosarcoma.

23. The method of claim 18 wherein the disease or medical condition is a tumor, selected from melanoma, seminoma, tetratocarcinoma, neuroblastoma and glioma.

* * * * *